(12) United States Patent
Tawil et al.

(10) Patent No.: US 11,937,953 B2
(45) Date of Patent: Mar. 26, 2024

(54) PORTABLE MEDICAL STATION

(71) Applicant: MEDPOD, INC., Melville, NY (US)

(72) Inventors: Jack Tawil, Brooklyn, NY (US); David Jack Tawil, Brooklyn, NY (US); Christopher Smith, Shirley, NY (US); Holland Bennett, Syosset, NY (US)

(73) Assignee: MEDPOD, INC., Melville, NY (US)

( * ) Notice: Subject to any disclaimer, the term of this patent is extended or adjusted under 35 U.S.C. 154(b) by 807 days.

(21) Appl. No.: 16/843,264

(22) Filed: Apr. 8, 2020

(65) Prior Publication Data

US 2020/0323605 A1    Oct. 15, 2020

Related U.S. Application Data

(60) Provisional application No. 62/833,552, filed on Apr. 12, 2019.

(51) Int. Cl.
| | |
|---|---|
| *A61B 50/13* | (2016.01) |
| *A61B 5/00* | (2006.01) |
| *A61B 8/00* | (2006.01) |
| *A61B 50/33* | (2016.01) |

(52) U.S. Cl.
CPC ............ *A61B 50/13* (2016.02); *A61B 5/0077* (2013.01); *A61B 5/7445* (2013.01); *A61B 8/4405* (2013.01); *A61B 50/33* (2016.02)

(58) Field of Classification Search
CPC ......... A61B 50/13; A61B 50/15; A61B 50/31; A61B 50/33; A61B 50/10; A61B 50/18; A61B 50/26; A61B 8/4427; A61B 5/044; A61B 5/021; A61B 5/0245; A61B 5/4803; A61B 5/7445; A61B 5/14; A61B 8/464; A61B 8/4408; A61B 7/02; A61B 2050/3008; A61B 2050/3011; A61B 2050/1311; A61B 5/0077; A61B 5/01; A61B 5/7405; A61B 5/02055; A61B 5/6887; A61B 5/7465; A61B 5/7495; A61B 8/4405; A61B 2560/0431; A61B 2560/0462; F61M 11/046; F61M 11/2201; F61M 11/38; F61M 11/42; G06F 1/1628; G06F 1/1674; A45C 13/28
USPC ............... 312/209, 223.3; 206/320; 190/115; 248/125.8, 917, 163.1, 186.6; 280/47.19, 280/47.26, 638, 652; 108/144.11, 145, 108/147, 147.22, 50.01, 50.02, 116, 115
See application file for complete search history.

(56) References Cited

U.S. PATENT DOCUMENTS

| | | |
|---|---|---|
| 5,255,187 A | 10/1993 | Sorensen |
| D346,658 S | 5/1994 | Bailey et al. |
| 5,796,862 A | 8/1998 | Pawlicki |

(Continued)

FOREIGN PATENT DOCUMENTS

WO    2008097862    * 8/2008

*Primary Examiner* — Janet M Wilkens
(74) *Attorney, Agent, or Firm* — Collard & Roe, P.C.; William Collard (57) ABSTRACT

At least one embodiment is a portable medical station comprising a main body, which is disposed at least partially inside of a bag. Coupled to the main body is at least one tray and a plurality of handles. There are also a plurality of screens coupled to the main body and at least one computer coupled to the main body, wherein the portable medical station is foldable inside of the bag so that the portable medical station is movable while being substantially folded inside of the bag.

15 Claims, 10 Drawing Sheets

(56) References Cited

U.S. PATENT DOCUMENTS

| | | | |
|---|---|---|---|
| 5,878,746 A | 3/1999 | Lemelson | |
| 6,543,796 B1 | 4/2003 | Johnson et al. | |
| 6,820,878 B2 | 11/2004 | Safari et al. | |
| 7,389,997 B2 | 6/2008 | Johnson et al. | |
| 7,551,755 B1 | 6/2009 | Steinberg | |
| 7,689,544 B2 | 3/2010 | Koenig | |
| D614,859 S | 5/2010 | Hansen | |
| D657,469 S | 4/2012 | Vilas | |
| 8,371,442 B1 * | 2/2013 | Pack | A45F 3/04 206/320 |
| 8,538,770 B2 | 9/2013 | Papier | |
| 8,540,109 B1 * | 9/2013 | McPeek | A45C 13/02 206/754 |
| 10,231,795 B1 * | 3/2019 | Johnson | A47B 97/00 |
| 10,588,709 B2 | 3/2020 | Johnson et al. | |
| 2004/0030232 A1 | 2/2004 | Barsky | |
| 2005/0216207 A1 | 9/2005 | Kermani | |
| 2006/0264714 A1 | 11/2006 | McGlennen | |
| 2007/0089648 A1 * | 4/2007 | Harrison | A47D 1/0085 108/115 |
| 2007/0094197 A1 | 4/2007 | Datena | |
| 2008/0215610 A1 | 9/2008 | De Lacharriere | |
| 2010/0222649 A1 | 9/2010 | Schoenberg | |
| 2012/0165647 A1 | 6/2012 | Kang | |
| 2012/0197660 A1 | 8/2012 | Prodanovich | |
| 2012/0325607 A1 | 12/2012 | Webster et al. | |
| 2015/0248536 A1 | 9/2015 | Tawil | |
| 2016/0183677 A1 | 6/2016 | Achillopoulos | |
| 2016/0295979 A1 | 10/2016 | Vincent et al. | |
| 2016/0367329 A1 | 12/2016 | Dekel | |
| 2017/0290413 A1 * | 10/2017 | Hu | A47B 9/16 |
| 2018/0303456 A1 * | 10/2018 | Tawil | A61B 5/7445 |
| 2019/0274773 A1 | 9/2019 | Johnson | |
| 2020/0205924 A1 * | 7/2020 | Johnson | F16M 11/38 |
| 2020/0237224 A1 * | 7/2020 | Sanchez | G16H 40/67 |
| 2020/0323605 A1 | 10/2020 | Tawil | |

\* cited by examiner

PORTABLE MEDICAL STATION

CROSS REFERENCE TO RELATED APPLICATIONS

This application is a non-provisional application that claims priority from U.S. Provisional Application Ser. No. 62/833,552 filed on Apr. 12, 2019, the disclosure of which is hereby incorporated by reference.

BACKGROUND OF THE INVENTION

At least one embodiment of the invention relates to a portable medical station configured to be collapsible into a single unit or which is capable of folding out into a more expansive station. It is believed that there is a need for a portable medical station that is configured to have multiple different screens and multiple different portable devices coupled to the portable medical station.

SUMMARY OF THE INVENTION

At least one embodiment of the invention is a portable medical station comprising a main body, which is disposed at least partially inside of a bag. Coupled to the main body is at least one tray and a plurality of handles. There are also a plurality of screens coupled to the main body and at least one computer coupled to the main body, wherein the portable medical station is foldable inside of the bag so that the portable medical station is movable while being substantially folded inside of the bag.

In at least one embodiment, the tray is rotatable about a hinge wherein the tray is foldable out from, or back into the main body. In at least one embodiment, there are a plurality of screens which comprise a first screen which is configured as a video screen coupled to the computer, and a second screen comprising a data readout screen coupled to the computer.

In at least one embodiment there is a spring configured to assist in the opening of the medical station from a bag.

In at least one embodiment, the main body comprises a frame which can be made from any material, but in at least one embodiment is aluminum.

In at least one embodiment, there is at least one peripheral device wherein the peripheral device can be any one of a stethoscope a thermometer, an ultrasound device, at least one camera, at least one speaker, and/or at least one blood pressure monitor.

In at least one embodiment, there is a plurality of arms extending out from the main body wherein a first end of the arms are coupled to the main body and a second end of the plurality of arms are coupled to the tray.

For example, the process can include opening a bag, and then removing at least one scale from the bag. Next the process can include pulling a handle and unfolding a tray from the bag. When the handle is pulled a spring such as a gas spring can be used to assist in the opening of the device from the bag. The tray can be rotated about a hinge and then locked in place. Supporting the tray are a plurality of arms extending up from the main body of the device. These plurality of arms can be locked in place via locks. Next, the user can raise at least one screen up and out from the bag. The screen can be rotated about a hinge and then locked in place by rotating a plurality arms out to a locked position. Next a main body can be raised up thereby raising a plurality of peripheral devices up and out from the bag. At least one camera can be placed upon a viewing position such as on top of a screen so that a remote medical professional can view a patient in a remote location. There can also be a process for collapsing the different devices into the bag as well. For example, the handles can be collapsed into the bag by pressing on one or more spring loaded detents. Next, the tray can be collapsed into the main body by pressing on at least one lever, which causes the plurality of locks to concurrently unlock the arms. This causes the tray to collapse into the main body.

Next, the screen can be rotated down and collapsed into the main body and the main body can be pressed into the remainder of the bag. Finally, the scale can be reinserted into at least one pocket on the bag as well to create a completely collapsed medical station.

Thus, this compact, portable device is configured to be connected to or connectable to multiple different peripheral devices while also being highly transportable as well. This device then allows medical professionals to conduct a relatively thorough exam on an individual. The camera in the system allows for remote medical professionals to interview and see a patient from a remote location as well.

With this design, full communication can be made between the patient and medical professionals who may be remote from this location. Therefore, it allows for a portable medical office to be transported within a standard sized bag such as a standard sized carry-on bag.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
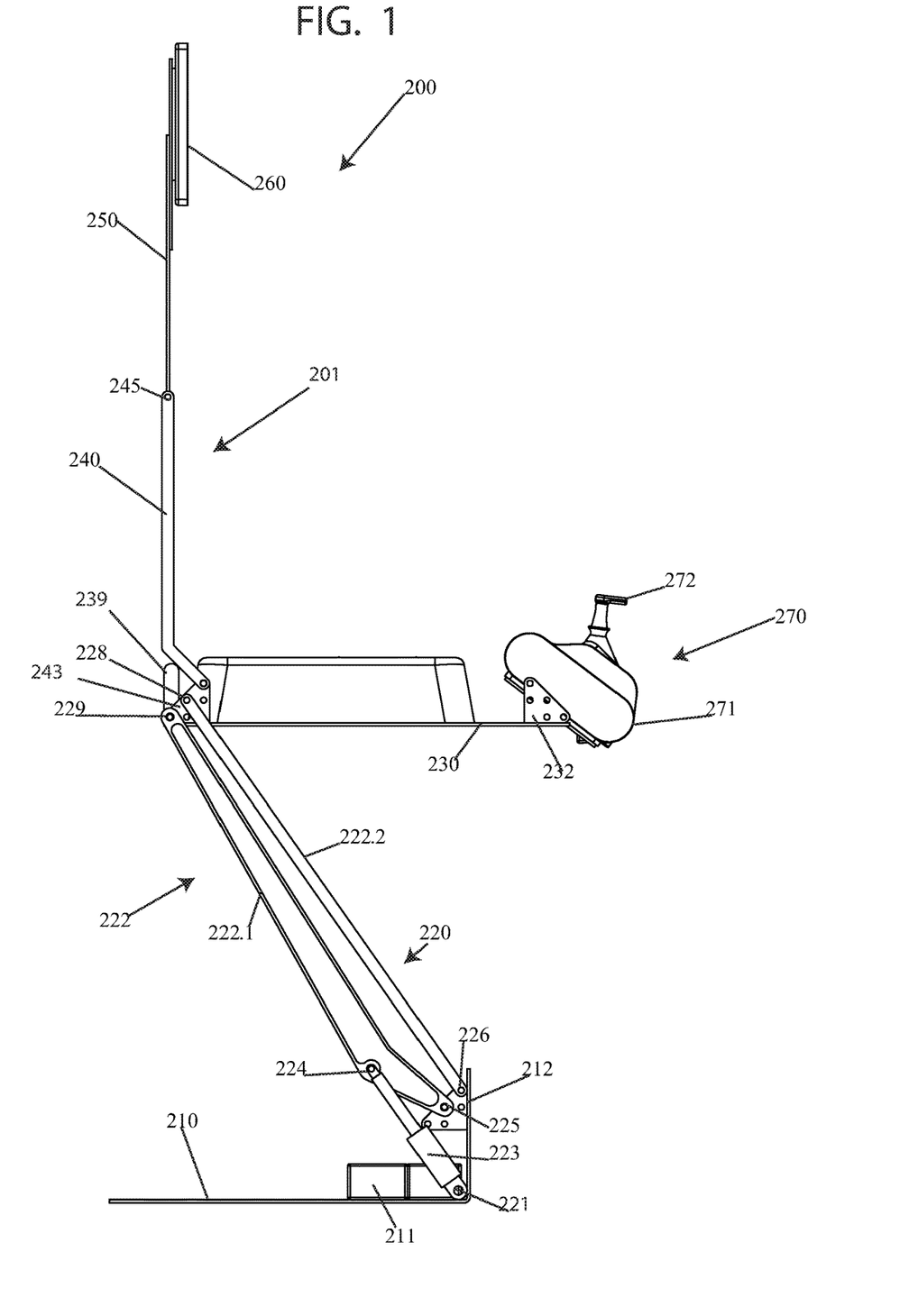
FIG. 1 is a side view of a portable medical station.

FIG. 1 shows another embodiment of the invention which relates to a portable mobile medical device or system 200. With this device there is a frame 201 which has a base 210 with a plurality of arms coupled to the base. In addition, there is a tray 230 and a screen 260 coupled to these arms. Inside of the tray or coupled to the tray 230 are a plurality of electronic and medical devices.

Coupled to base 210 is a power supply 211 which in one embodiment is a transformer configured to receive power from an outlet. In at least another embodiment, this power supply 211 is a battery pack and transformer combination. Coupled to base 210 is a first hinge 221.

A spring such as a gas spring or piston 223 is coupled to hinge 221. Gas spring or piston 223 is configured to aid in the opening and closing of the device by biasing the station into an open position when a handle 239 is pulled when the device is in a closed position. At an opposite end to hinge 221 is another hinge 224. Arms 222 comprise arms 222.1 and 222.2. Arm 222.1 is coupled at a first end to hinge 224 and at a second end to hinge 229. Arm 222.1 is also coupled to a bracket 212 via hinge 225. Bracket 212 is a triangular shaped bracket that has at least two hinges 225 and 226 coupled to it. Thus arm 222.1 is coupled at one end via two different hinges 224 and 225. Arm 222.1 is thus angled so that the hinges 224 and 225 are offset from each other.

Arm 222.2 is coupled at one end to hinge 226 and at another end to hinge 228. Hinge 226 is coupled to bracket 212. Hinge 228 is also coupled to another substantially triangularly shaped bracket 243 as well. Bracket 243 also has hinge 241 coupled to it as well as tray 230 coupled to it as well. Tray 230 is essentially in the form of a table when extended out. While tray 230 is coupled at one end to bracket 243, it is coupled to another substantially triangularly shaped bracket 232 at another end. In addition, a handle 239 is coupled to bracket 243 as well.

A set of arms 240 comprising upper arms when the device is in an extended position extend out from bracket 243. Arms 240 comprise a first set of arms 242 and a second set of arms 244 (See FIG. 2). Arms 240 are coupled at a first end to hinge 241 and at a second end to hinge 245. A bracket 250 is coupled at a first end to hinge 245 and at a second end to screen 260.

In addition, there are a plurality of medical devices 270 coupled to bracket 232. These medical devices include a at least a central computer 271, and a probe 272.

Figure 2:
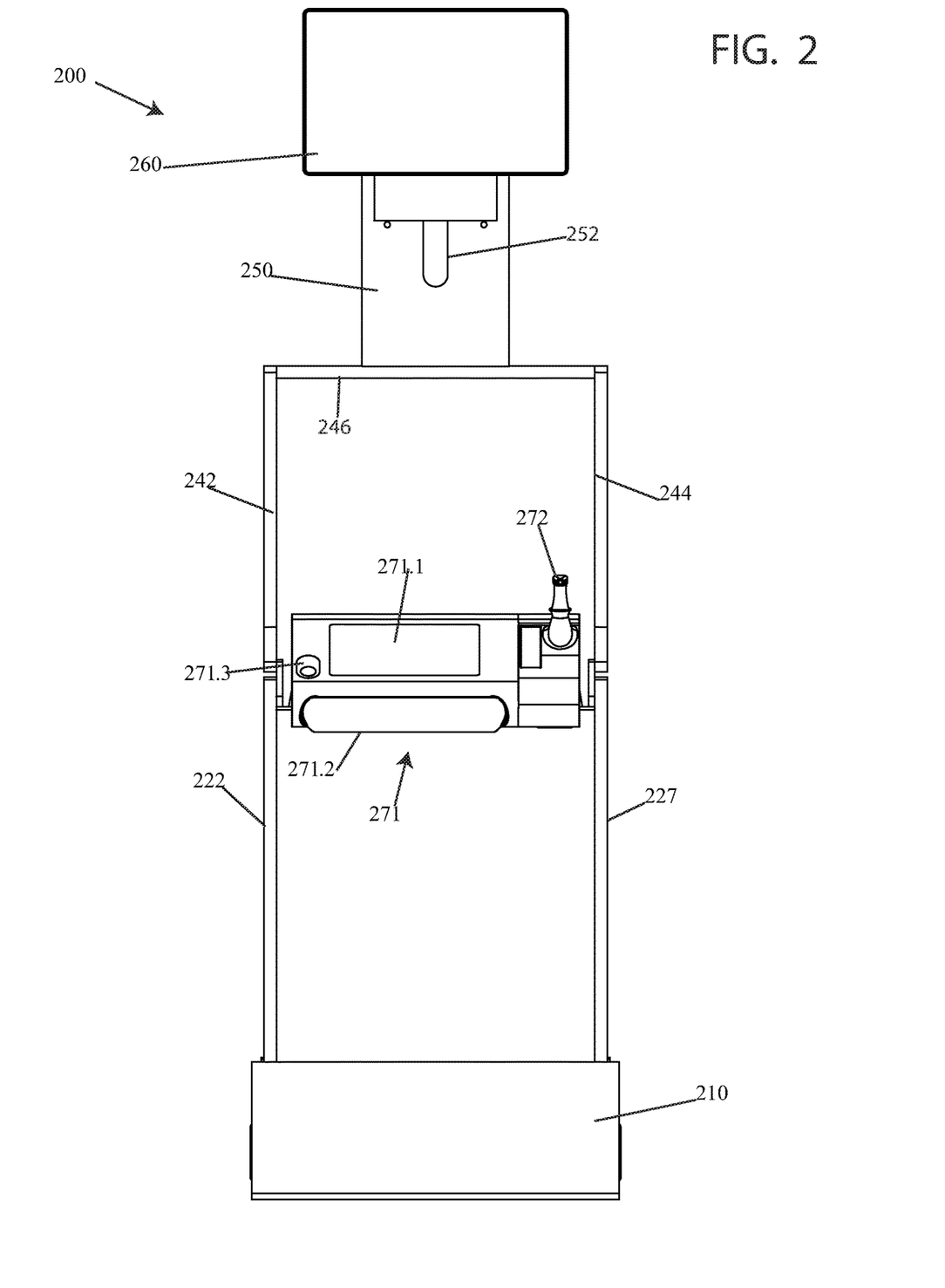
FIG. 2 is a front view of a portable medical station.

FIG. 2 is a front view of the device 200 which shows base 210 with arms 222 and 227 extending up therefrom. Arms 227 comprise arms 227.1 and 227.2 (See FIG. 3) wherein arms 227 are substantially identical to arms 222. There is shown central computer 271 having a pull out keyboard 271.2, and an on-off switch 271.3. Probe 272 is in communication with central computer 271 and is in communication with computer 271 in either a wired or wireless manner.

This view also shows arms 242 and 244 extending up to bracket 250. Bracket 250 has a slot 252 which allows screen 260 to be moved up or down.

Figure 3:
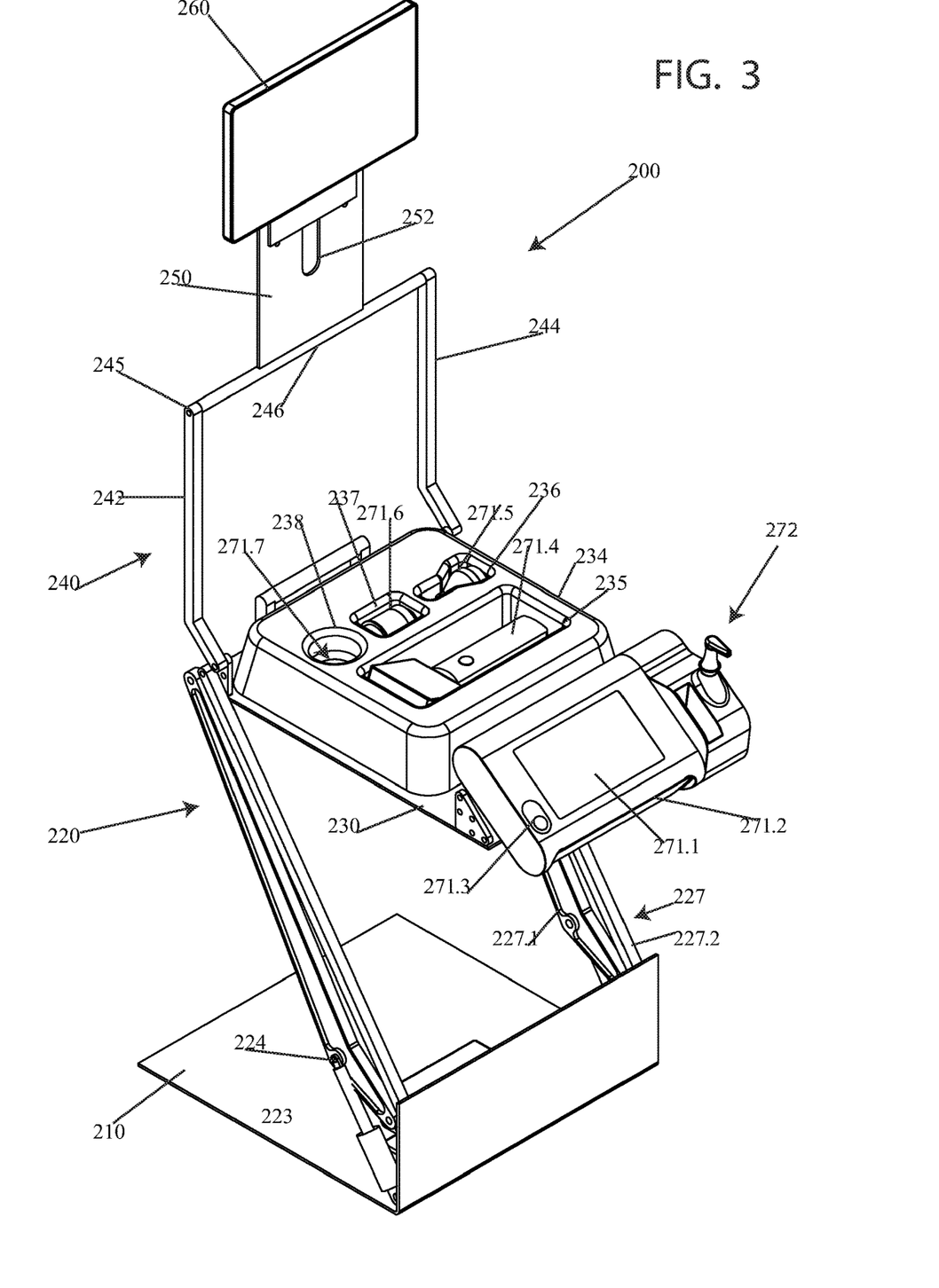
FIG. 3 is a perspective view of a portable medical station.

FIG. 3 shows a top perspective view of the device 200 which shows both arms 222 and 227. This view also shows central computer 270 having a touch screen panel 271.1 and an on-off switch 271.3. Probe 272 is coupled to the central computer 270. In this view tray 234 is shown coupled to tray or table 230. Tray 234 has a plurality of containers such as a first container 235, a second container 236, a third container 237, and a fourth container 238.

Inside of each of these containers are peripheral medical devices such as a first peripheral medical device 271.4, a second peripheral medical device 271.5 a third peripheral medical device 271.6 and a fourth peripheral medical device 271.7. These different peripheral medical devices can include any one of a stethoscope, a thermometer, an ultrasound, a camera, a speaker and a blood pressure monitor.

A handle 239 is shown positioned adjacent to tray 234. As indicated above, when handle 239 is pulled up, it causes arms 222 and 224 to rotate clockwise about hinges 221, 225 and 226 while tray 230 rotates counter clockwise about hinge 229 away from arms 222 and 224. Meanwhile arms 240 including arms 242 and 244 rotate counter clockwise relative to hinge 241 thereby allowing for the opening of screen 260. Bracket 250 is rotatable about hinge 245 so that the screen can remain visible. Screen 260 can be in the form of a tablet such as a tablet computer. The tablet computer can comprise a microprocessor, a microphone, speakers, a camera and a screen.

In addition, coupled to arms 242 and 244 is an arm/cross beam 246 which is coupled to arms 242 and 244 via a hinge 245. Screen 260 is slidable in a slot 252 so that the entire device can be expanded up or easily collapsed down and then carried via handle 239. Base 210 then provides a cover for the collapsed device. This device can be fit inside of a bag and even coupled to a bag as well. The bag can be configured to have rolling wheels as well.

Figure 4:
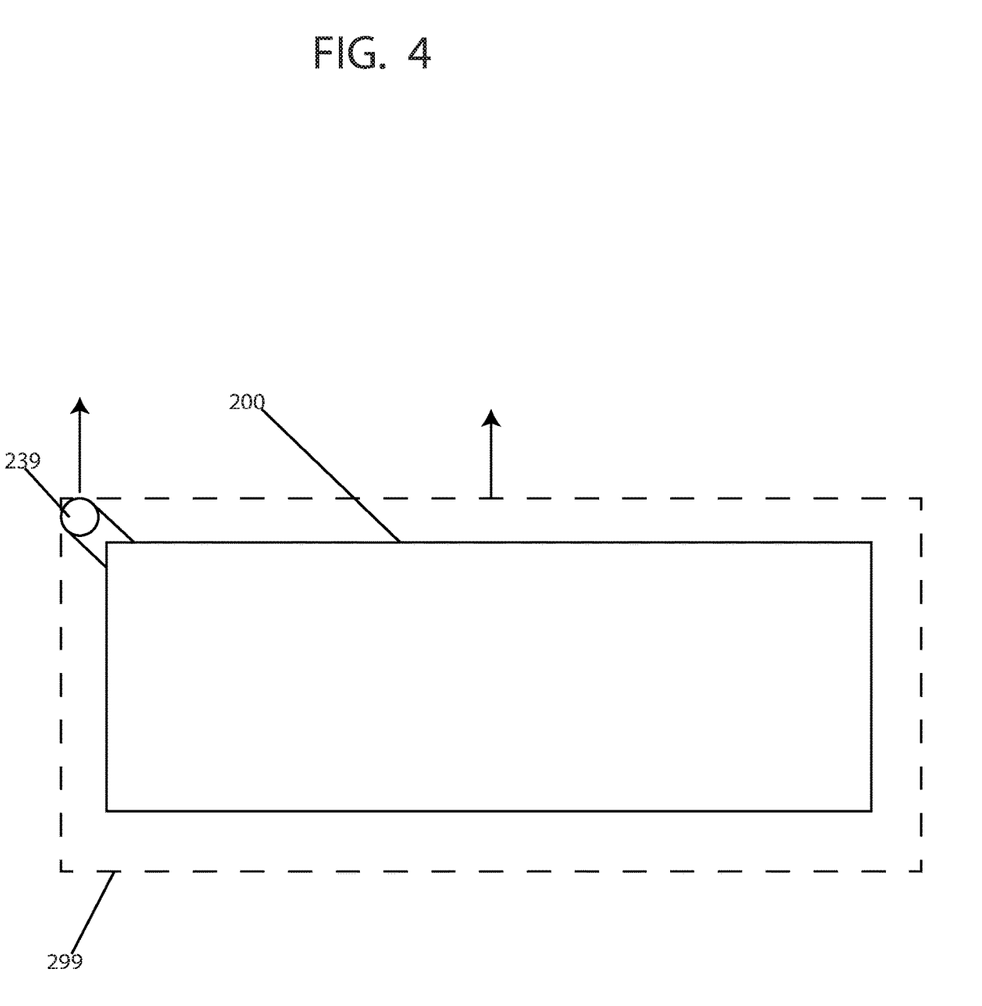
FIG. 4 is a side view of the collapsed view of the portable medical station.

FIG. 4 shows the collapsed version of the device 200 disposed inside of a bag 300. The device is designed to either be transportable separate from a bag or collapsible inside of a bag. So that the device is easily openable and closable the device can rely on the spring such as gas spring 223 to either assist a user in opening up the device or closing the device in a more controlled manner. For example, when the user pulls on a handle in a direction shown by the arrow such as handle 239, the spring such as spring 223 is biased once it is moving to push open the arms 222 and 224 so as to raise up tray 230 and to allow for the extension of arms 240 so that the screen 260 and other components are is raised up and out of a bag such as bag 299.

Figure 5:
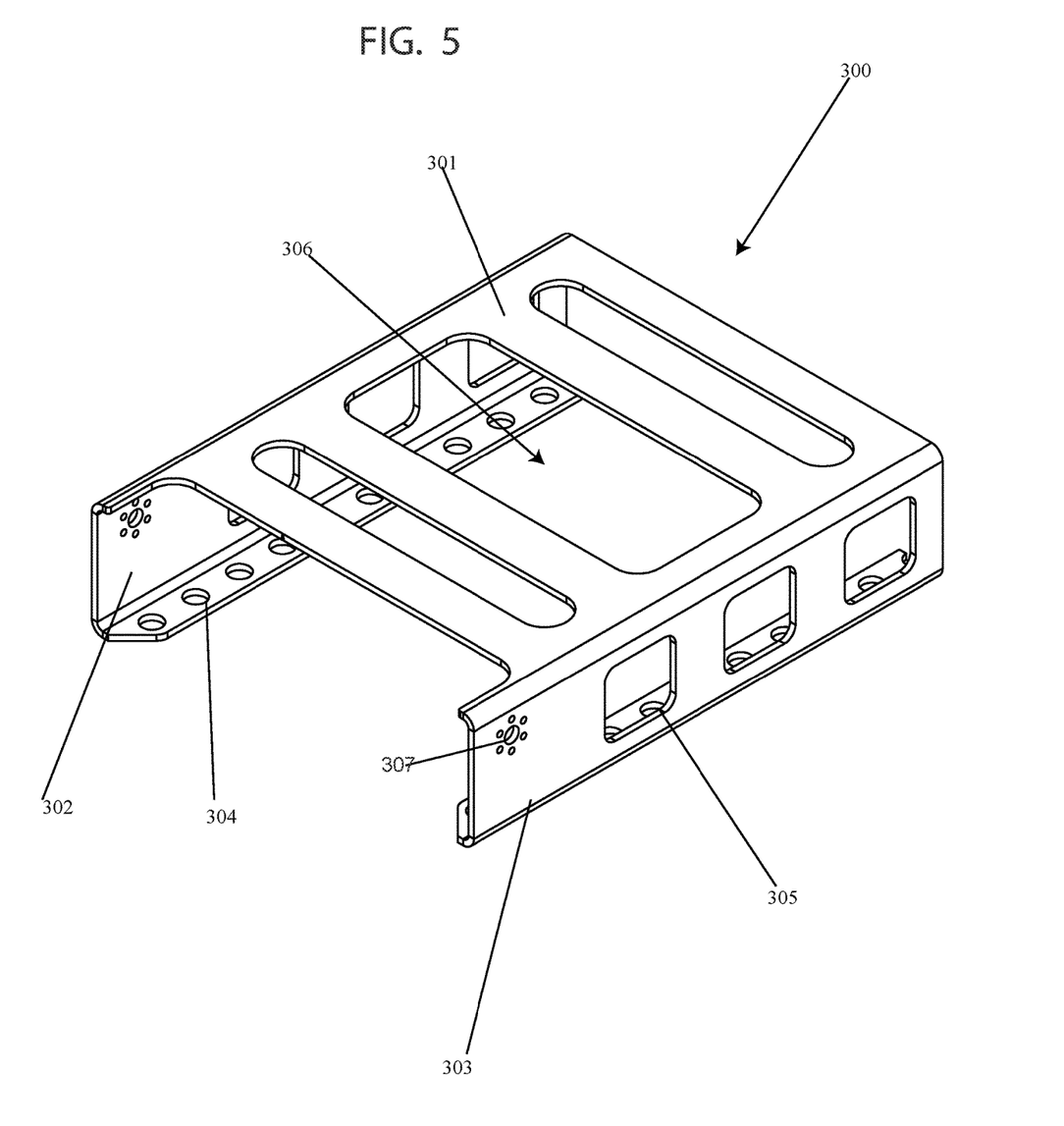
FIG. 5 is a perspective bottom view of a bag mount bracket.

FIG. 5 is a bottom perspective view of a back mount bracket 300 which can be coupled to a bag such as bag 299. This bracket includes a base wall 301, and openings 305 and 306 to reduce the weight of the bracket. There are also side walls 302, and 303 as well as mounting holes which include a hole 304 as well as an axle hole 307 for allowing arms such as arms 222 to be coupled thereto. For example, this bracket 300 can take the place of bracket 211 and be coupled to base 210 wherein axle hole 307 is coupled to hinge 221.

Figure 6:
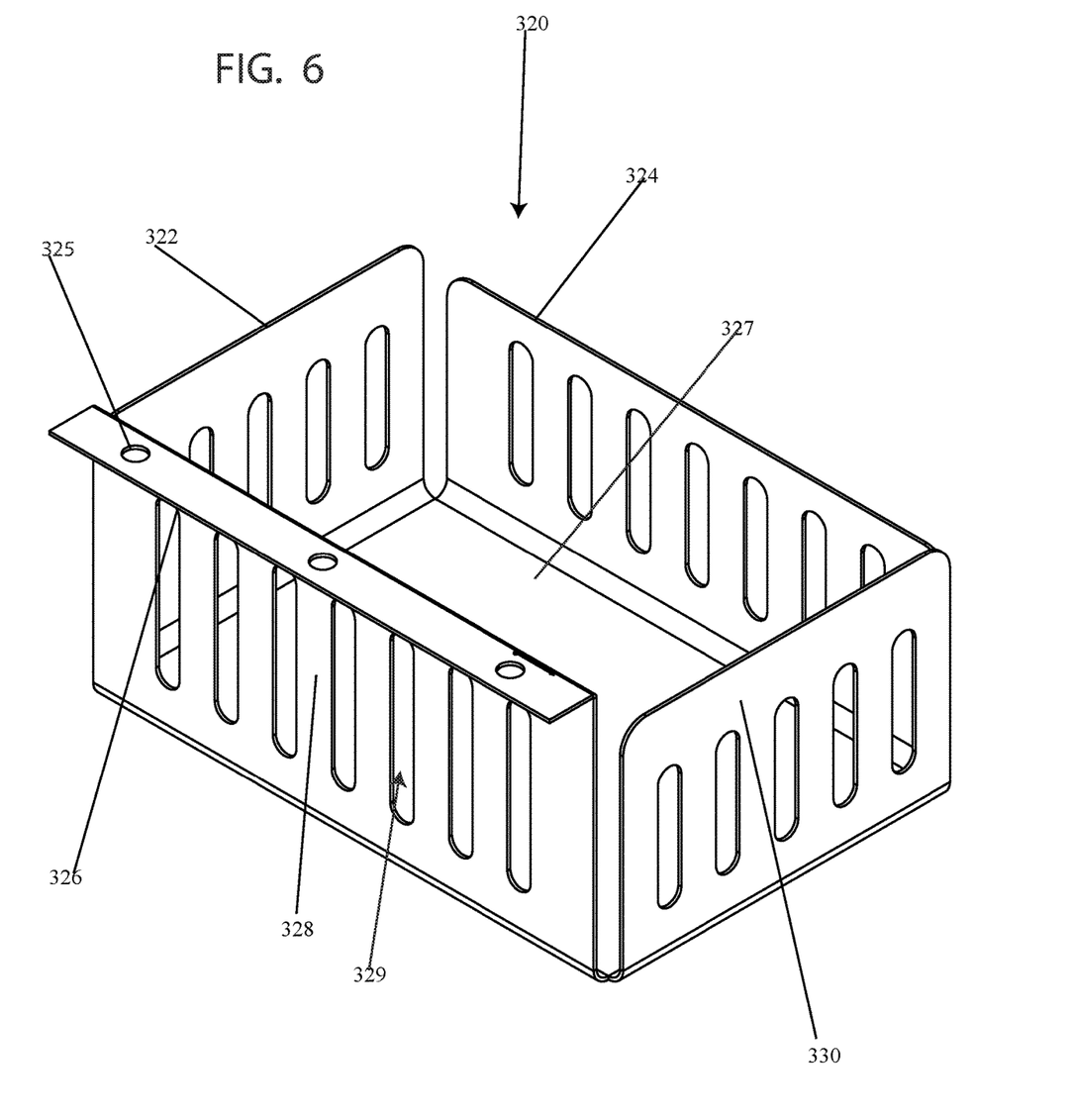
FIG. 6 is a perspective view of an instrument mount bracket.

FIG. 6 is a side perspective top view of a instrument mount basket 320. This instrument mount basket includes a base section 327 for receiving objects. In addition, there are side walls 322 and 330 as well as walls 324 and 328. There is also a back mounting flange 326 with mounting holes 325 disposed therein. These mounting holes are configured to allow the device to be mounted onto either arms 240 or onto screen back panel shown in FIG. 9.

Figure 7:
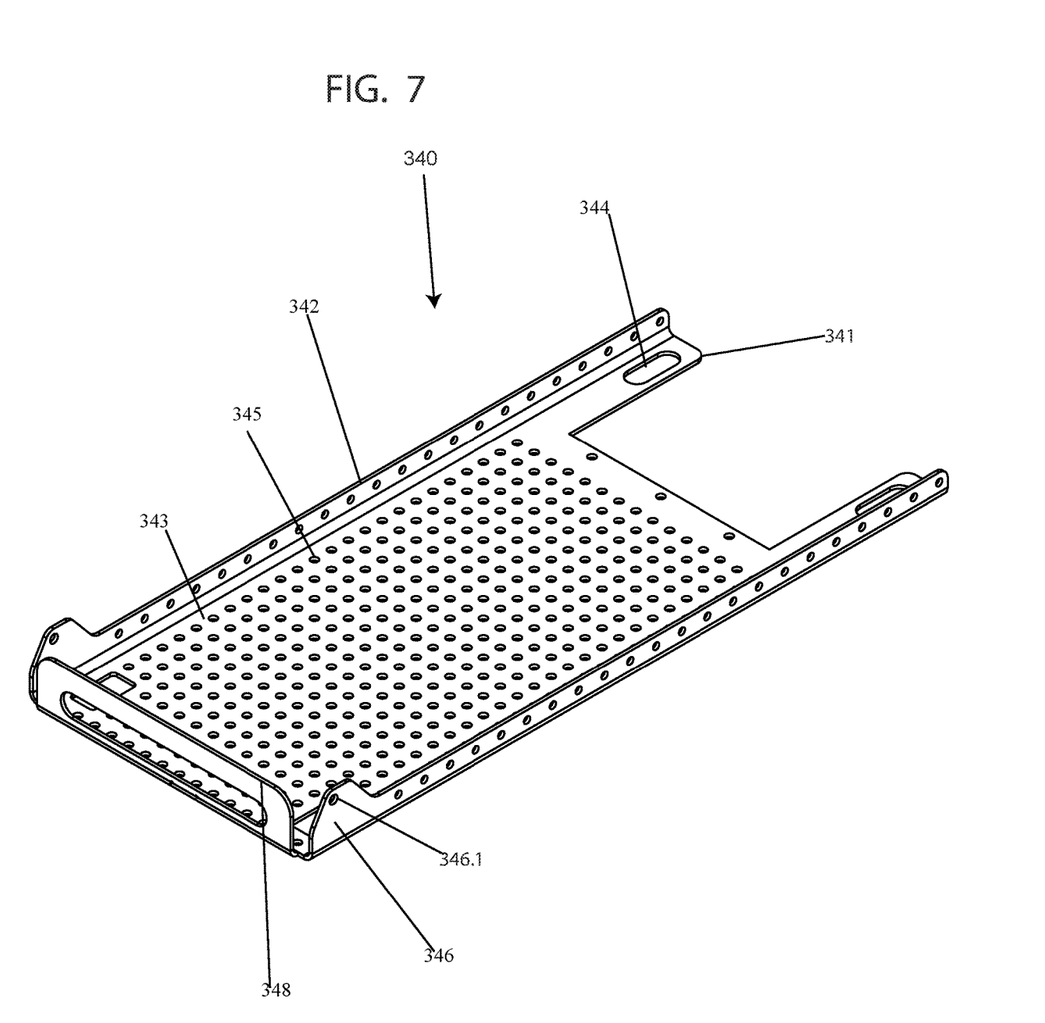
FIG. 7 is a perspective view of a tray.

FIG. 7 shows a first tray 340 which is configured to essentially replace tray 230 and be mounted to bracket 243. This tray has a front-end section 341, a body section 343, and side walls 342. In the front-end section is a mounting hole 344 to allow tray 350 to mount thereto with an angle bracket such as a gusset shown in FIG. 10. In the back end of tray 340 is a hinge section 346 having a hinge hole 346.1 for coupling to bracket 343 and/or arms 222. A back-end flange 348 extends substantially perpendicular to the extension of body section 343 and has a hole or slot positioned on this back end.

Figure 8A:
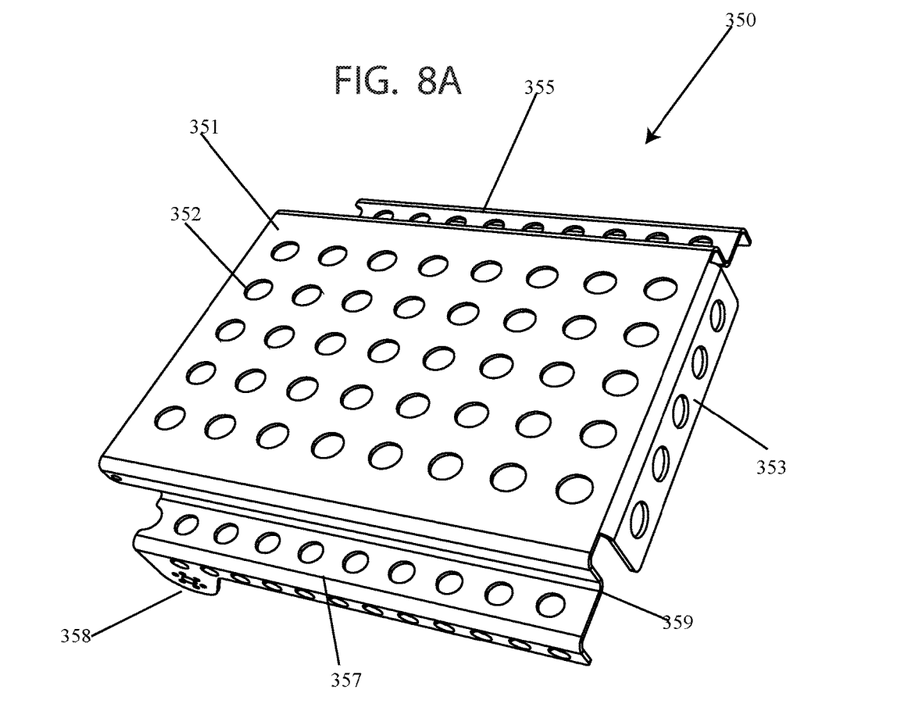
FIG. 8A is a perspective bottom view of a tray.
Figure 8B:
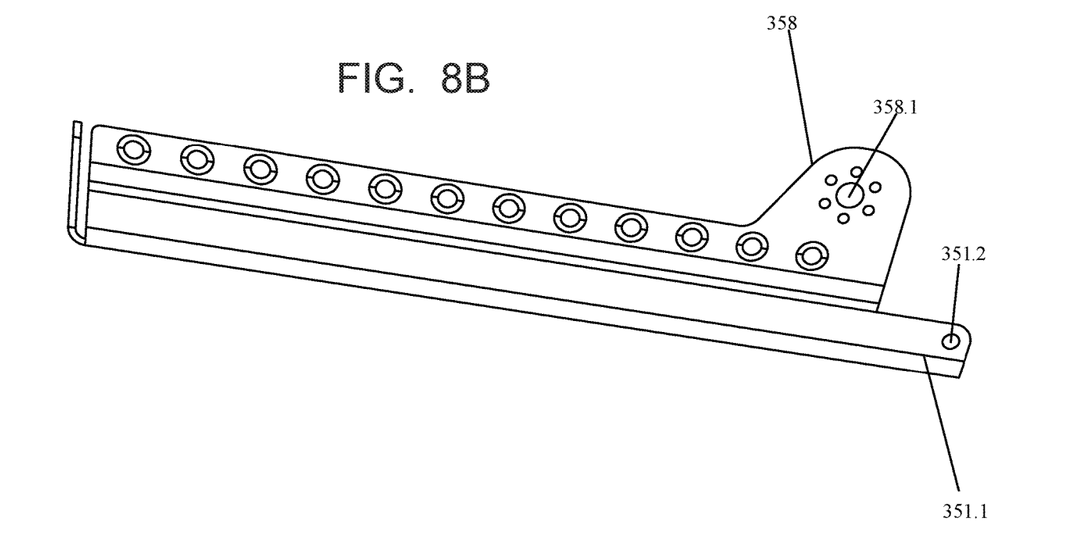
FIG. 8B is a side view of a tray.

FIGS. 8A and 8B is a bottom perspective view and a side view of another tray such as a medical device and/or computer tray. This tray is configured to receive a computer 270 and to be rotatable vs. tray 340 via hinge 358. For example, tray 350 includes a base 351, holes 352, an end bracket 353. End bracket 353 is configured to keep computer 270 therein. In addition, there are arms 355 and 357 which have angled bend points 359 such that these arms 355 and 357 form side walls and open surfaces for additional mounting. As shown in FIG. 8B hinge 358 includes a hinge hole 358.1 while there is also an extension section 351.1 having an additional hinge hole as well. Coupling tray 350 to tray 340 is a gusset such as bracket 232. Holes 358.1 and 351.1 are used to secure to a bracket 232 which then allows for this tray 350 to be secured to tray 340.

Figure 9:
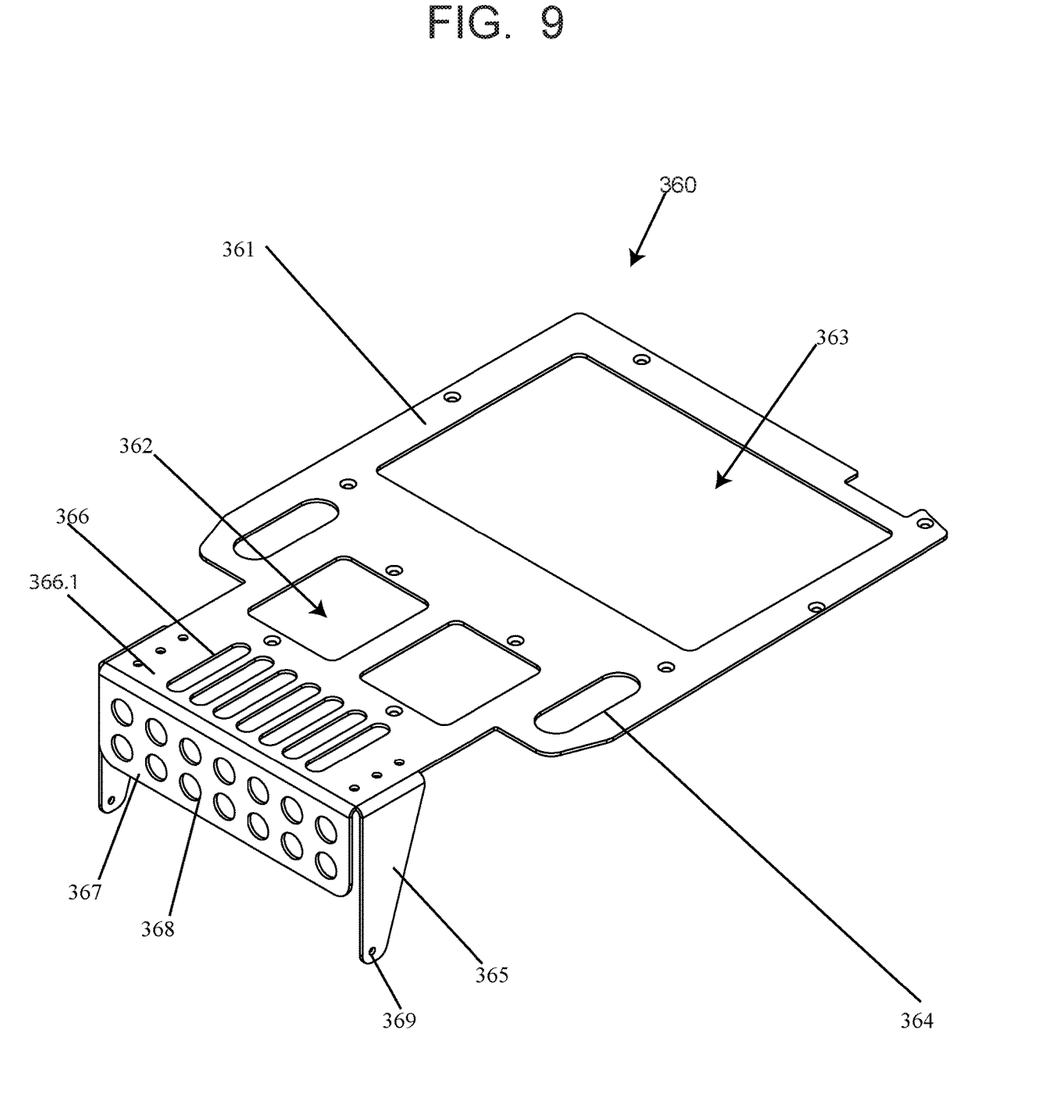
FIG. 9 is a perspective view of a monitor or screen back panel.

FIG. 9 is a back perspective view of a screen back panel 360 which can be used to replace a panel such as panel 250 to support a screen such as screen 260. This screen back panel 360 includes a frame section 361, a hole or open section 363 for receiving a screen, openings 362 are configured to form open areas to receive additional components, while slots 366 are also formed to allow other trays or devices to attach thereto. There is a narrowed bottom bracket section 366.1 which is coupled to frame section 361 and which has hinge section 365 having hinge opening 369 coupled to hinge section 365. A bottom flange section 367 has a plurality of holes 368 formed therein to form a shelf at the bottom of the screen back panel. Opening 369 is configured to form a hinge connection such that the screen back panel can be coupled to either arms 240 in a hinge like manner or to an adjacent bracket 243.

Figures 10A, 10B:
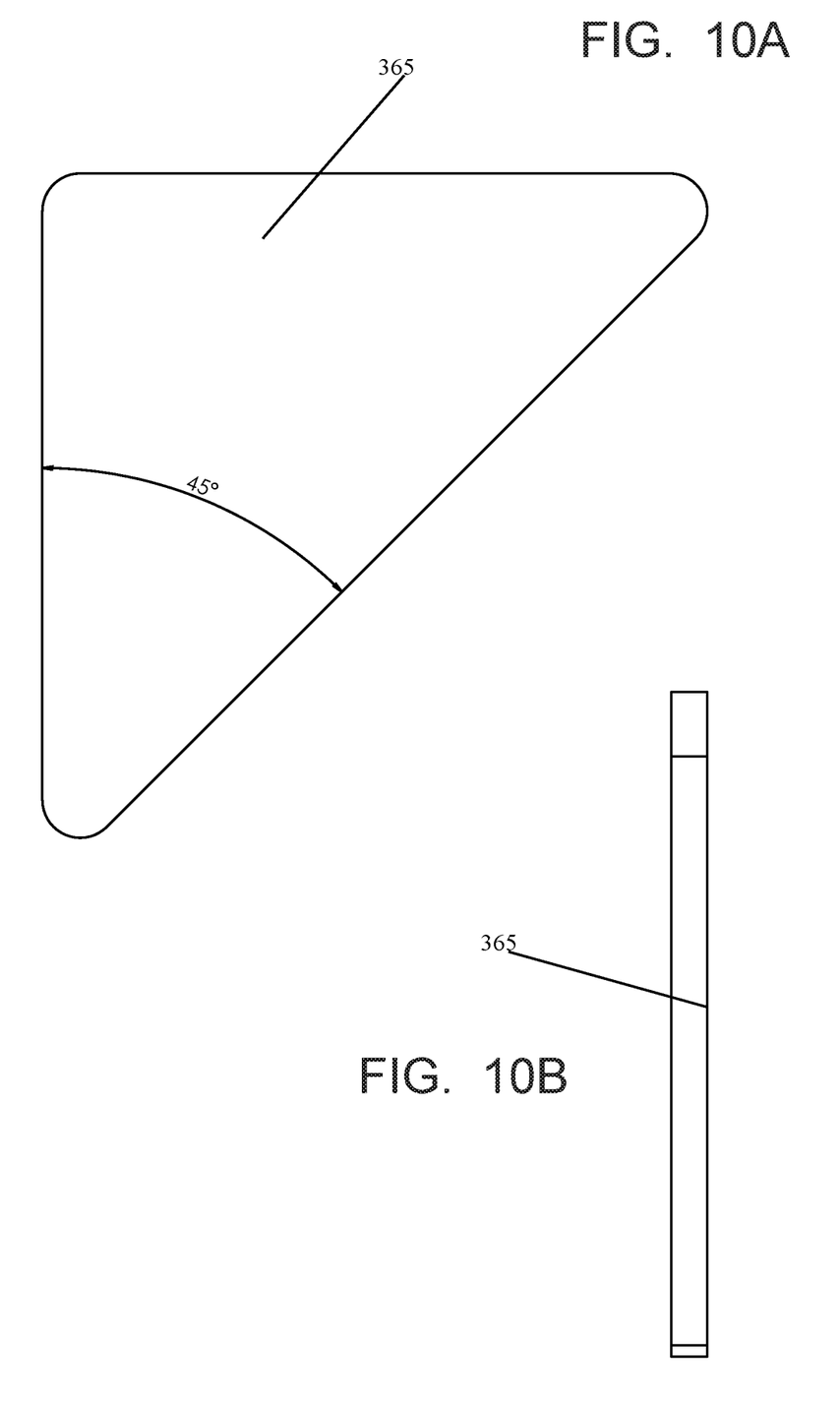
FIG. 10A is a side view of a gusset.
FIG. 10B is an end view of a gusset.

FIG. 10A shows a side view of a gusset 375 while FIG. 10B shows an end view of a gusset 375 which is configured to receive a plurality of holes wherein gusset 375 is configured to selectively replace bracket 243, or bracket 232.

In all, the different embodiments of the invention provide for a mobile, collapsible transportable device which can be used to provide extensive medical examinations to different personnel.

Accordingly, while at least one embodiment of the present invention have been shown and described, it is to be understood that many changes and modifications may be made thereunto without departing from the spirit and scope of the invention as defined in the appended claims.

What is claimed is:

1. A portable medical station comprising:
   a bag;
   a main body comprising a frame;
   a plurality of arms coupled to said frame;
   a tray coupled to the plurality of arms;
   at least one handle coupled to the plurality of arms;
   at least one screen coupled to the plurality of arms;
   at least one computer coupled to the tray,
   at least one spring coupled to the main body, and to said plurality of arms wherein said spring is configured to aid in opening and closing said plurality of arms into said bag; and
   wherein the main body, the plurality of arms, the tray, the screen, the at least one computer and the at least one spring are configured to fit inside of said bag so that the portable medical station is movable while being substantially stored inside of said bag.

2. The portable medical station as in claim 1, further comprising a plurality of tray arms and a tray hinge, wherein said tray is foldable out from said main body via said tray hinge.

3. The portable medical station as in claim 1, wherein said at least one screen comprises a plurality of screens which comprise a first screen which is configured as a video screen coupled to said at least one computer, and a second screen comprising a data readout screen coupled to said at least one computer.

4. The portable medical station as in claim 1, further comprising at least one peripheral device.

5. The portable medical station as in claim 4, wherein said at least one peripheral device comprises at least one stethoscope.

6. The portable medical station as in claim 4, wherein said at least one peripheral device comprises at least one thermometer.

7. The portable medical station as in claim 4, wherein said at least one peripheral device comprises an ultrasound device.

8. The portable medical station as in claim 4, wherein said at least one peripheral device comprises at least one camera.

9. The portable medical station as in claim 4, wherein said at least one peripheral device comprises at least one speaker.

10. The portable medical station as in claim 4, wherein said at least one peripheral device comprises at least one blood pressure monitor.

11. The portable medical station as in claim 1, wherein said plurality of arms comprises a first set of arms and a second set of arms, wherein for said first set of arms, a first end is coupled to said main body and a second end of said first set of arms is coupled to said tray.

12. The portable medical station as in claim 11, wherein for the second set of arms, a first end is coupled to said tray and a second end is coupled to said screen.

13. The portable medical station as in claim 1, wherein said at least one screen comprises a tablet computer.

14. The portable medical station as in claim 1, wherein said spring is a gas spring.

15. The portable medical station as in claim 1, wherein said spring is a piston.

* * * * *